(12) United States Patent
Campista

(10) Patent No.: US 9,307,945 B2
(45) Date of Patent: Apr. 12, 2016

(54) MEDICAL EQUIPMENT PROTECTION DEVICE(S)

(76) Inventor: Amos J. Campista, Clarkdale, AZ (US)

( * ) Notice: Subject to any disclaimer, the term of this patent is extended or adjusted under 35 U.S.C. 154(b) by 1032 days.

(21) Appl. No.: 13/422,431

(22) Filed: Mar. 16, 2012

(65) Prior Publication Data

US 2013/0240402 A1 Sep. 19, 2013

(51) Int. Cl.
*A61B 6/00* (2006.01)
*A61B 19/08* (2006.01)
*B32B 7/12* (2006.01)
*B32B 27/12* (2006.01)

(52) U.S. Cl.
CPC .............. *A61B 6/4423* (2013.01); *A61B 19/081* (2013.01); *A61B 19/088* (2013.01); *B32B 7/12* (2013.01); *B32B 27/12* (2013.01); *A61B 6/4441* (2013.01); *B32B 2307/51* (2013.01); *B32B 2307/726* (2013.01); *B32B 2556/00* (2013.01); *Y10T 428/13* (2015.01); *Y10T 428/18* (2015.01); *Y10T 428/192* (2015.01)

(58) Field of Classification Search
CPC ........ A61B 19/08; A61B 19/081; A61B 6/10; A61B 6/4423; A61B 6/4441; A61B 19/088; B32B 7/12; B32B 27/12; B32B 2307/51; B32B 2307/726; B32B 2556/00; B32B 19/088; Y01T 428/13; Y01T 428/18; Y01T 428/192

See application file for complete search history.

(56) References Cited

U.S. PATENT DOCUMENTS

| | | | |
|---|---|---|---|
| 6,725,893 B1* | 4/2004 | Erickson | A61B 19/0248 150/154 |
| 2003/0056698 A1* | 3/2003 | Comeaux | A47G 11/004 108/90 |
| 2009/0200143 A1* | 8/2009 | Hahnel | H01H 3/14 200/86.5 |
| 2011/0035003 A1* | 2/2011 | Preissman | A61F 2/12 623/7 |
| 2011/0041995 A1* | 2/2011 | Adams | A61B 19/026 156/250 |

OTHER PUBLICATIONS

Preferred Medical Products, Medical Equipment Covers brochure, 2012, p. 7, 10, 11.*

* cited by examiner

*Primary Examiner* — Glen Kao
*Assistant Examiner* — Chih-Cheng Kao
(74) *Attorney, Agent, or Firm* — Jason C. Beckstead

(57) ABSTRACT

Medical equipment protection material including an adhesive layer, an absorbent layer, and a splatter shield.

17 Claims, 8 Drawing Sheets

MEDICAL EQUIPMENT PROTECTION DEVICE(S)

FIELD

The subject technology generally relates to medical equipment protection material(s).

BACKGROUND

For many operating room personnel, clean-up following surgery is time-consuming and potentially hazardous. The human body, being comprised substantially of water, can excrete large quantities of fluid during surgery. Blood is approximately 90% water. The brain and muscles are approximately 75% water. Bones and cartilage are about 20% water.

Despite the best efforts of operating room staff and professionals, human fluids often end up all over operating room equipment. For example, C-arm x-ray radiology equipment, when rotating an x-ray transmitter at one end of a structural C-arm for examination of the human body by a doctor performing surgery, places an x-ray receptor at the opposite end of the C-arm from the x-ray transmitter. Many C-arm x-ray machines rotate approximately 240 degrees to allow doctors to see in two planes as they examine and/or perform surgeries. Rotating the equipment to allow for varied views and/or access to the subject being operated on virtually guarantees that human fluids, e.g. blood, will end up at least somewhere on the C-arm and/or other portions of the equipment.

Cleaning up human fluids is time consuming. It can also be dangerous. Sometimes blood dries on the equipment and in the process of removal dried blood particles becomes airborne. Blood can carry many types of pathogens, and exposure to clean-up crews may cause disease. One objective of the subject technology is to minimize the time needed for cleanup and/or to limit clean-up crews' exposure to human fluids.

SUMMARY

The subject technology addresses the previous problems by providing medical equipment protection material(s) that both protect medical equipment and allow for safe, time-efficient clean-up post-surgery. Individual embodiments of the instant invention may include all of the elements of the claims and written description as provided herein, or a portion or portions of the element(s) of the claims and written description as provided herein.

In accordance with an embodiment of the subject technology, medical equipment protection material is provided including a first layer with a flexible, fluid-absorbent material having at least one edge; a second layer having an adhesive face; and a flexible wing edging. The first layer and the second layer are layered one atop the other such that the fluid-absorbent material is open-faced on a side opposite of the medical equipment protection material from the adhesive face of the second layer. The flexible wing edging abuts the at least one edge and projects past the at least one edge.

Additional embodiments include having at least one structural arm that supports the flexible wing edging past the at least one edge. The flexible wing edging may be made of a thin plastic film. The flexible wing edging may abut at least two edges of the fluid absorbent material. The second layer along with the flexible wing edging form a contiguous liquid barrier.

Further embodiments include flank portions of the medical protection material that cover side surfaces of medical equipment, the flank portions folding out or unrolling from a main portion of the medical protection material. The flank portions may be connected with an elastic band that holds the flank portions against the side surfaces. In some embodiments, the flank portions form a sock for holding the medical protection material, either for clean-up or for storage of the medical equipment protection material prior to its use. The invention may include a "shower cap" type of plastic covering that may be located opposite of the flank portions or at the same end as the flank portions, for at least one of covering the medical equipment being protected and/or for storing the medical equipment protection material post-use for disposal.

In certain embodiments, the flexible wing edging projects past the at least one edge at least as far as handles extend from the medical equipment being protected, for example, handles on a C-arm x-ray machine. The invention may include a tubular fluid barrier for containing cords from the medical equipment, and the tubular fluid barrier may include at least one suction cup for affixing the tubular fluid barrier to a surface, for example, the floor of an operating room. The tubular fluid barrier may include a fluid-absorbent material on an exterior surface. The tubular fluid barrier may include fluid absorption material connected to an end of the tubular fluid barrier for covering foot switch controls connected to the medical equipment with the cords. The fluid absorption material connected to the end of the tubular fluid barrier may include a graphic or graphics on the fluid absorption material connected to the end of the tubular fluid barrier, the graphic or graphics noting a type or types of foot switch control(s). The fluid absorption material connected to the end of the tubular fluid barrier may comprise a bag that fits over foot switch controls.

In some embodiments, the flexible wing edging is malleable with the human hand and is shape-retentive when bent. The medical equipment protection material may include at least one of the first layer and the second layer comprising a rip-stop material with interwoven threads in a crosshatch pattern. Certain embodiments of the invention include sterile packaging for storing the medical equipment protection material.

The medical equipment protection material may include at least one support strap for attaching the medical equipment protection material to the medical equipment.

Additional features and advantages of the subject technology will be set forth in the description below, and in part will be apparent from the description, or may be learned by practice of the subject technology. The advantages of the subject technology will be realized and attained by the structure particularly pointed out in the written description and claims hereof, as well as the appended drawings.

It is to be understood that both the foregoing general description and the following detailed description are exemplary and explanatory and are intended to provide further explanation of the subject technology as claimed.

BRIEF DESCRIPTION OF THE DRAWINGS

The accompanying drawings, which are included to provide further understanding of the subject technology and are incorporated in and constitute a part of this specification, illustrate aspects of the subject technology and together with the description serve to explain the principles of the subject technology. The features and nature of the present disclosure will become more apparent from the detailed description set forth below when taken in conjunction with the drawings in which like reference characters identify correspondingly throughout and wherein.

DETAILED DESCRIPTION

In the following detailed description, numerous specific details are set forth to provide a full understanding of the subject technology. It will be obvious, however, to one ordinarily skilled in the art that the subject technology may be practiced without some of these specific details. In other instances, well-known structures and techniques have not been shown in detail so as not to obscure the subject technology. The instant invention and technology may be used in either of a sterile or non-sterile environment.

Figure 1:
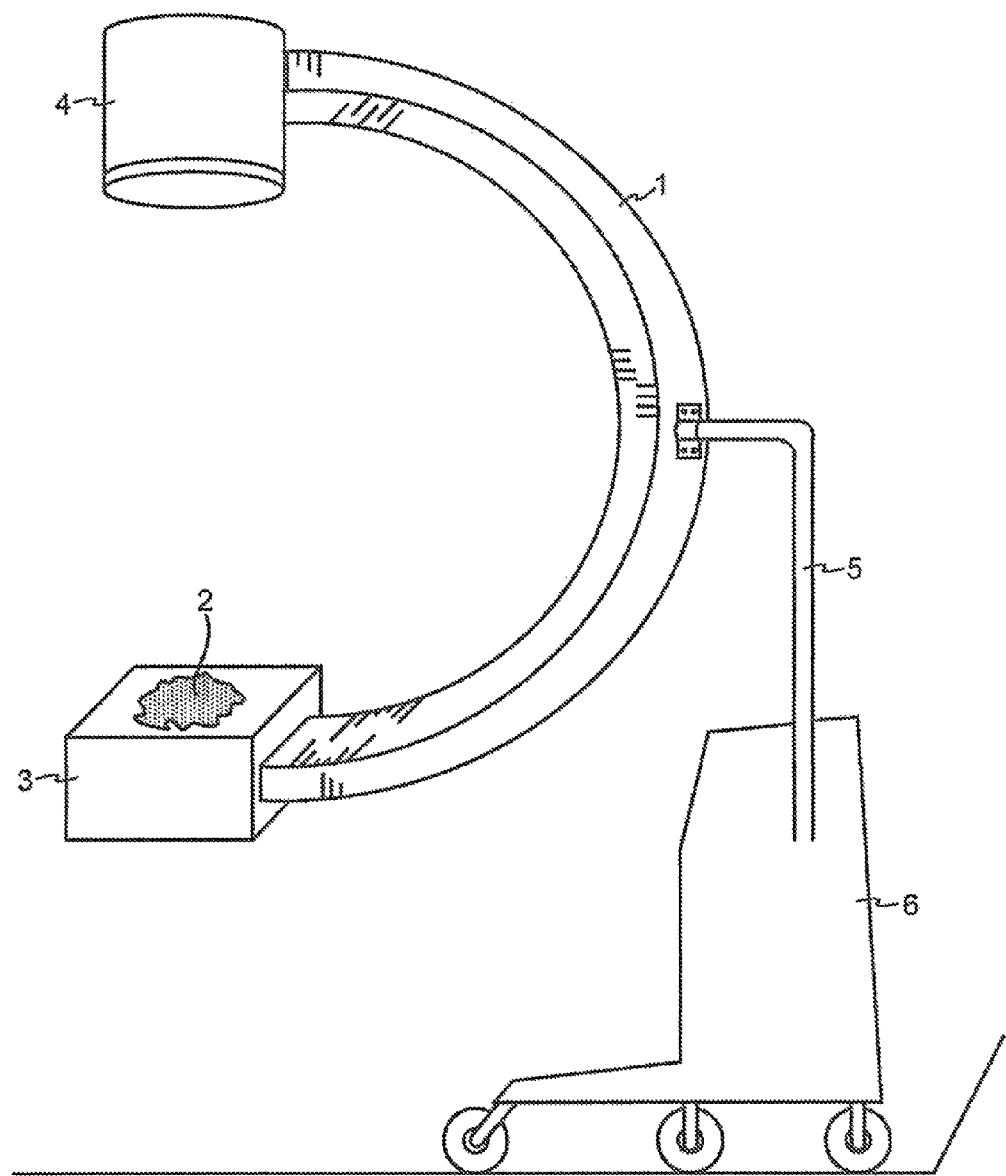
FIG. 1 is an illustration of a C-arm medical x-ray device.

FIG. 1 is an illustration of a C-arm 1 medical x-ray device with transmitter 3 and image intensifier 4. Supporting C-arm 1 is support 5. Support 5 provides for C-arm 1's movement through approximately up to 240 degrees in a semi-circular motion. It is understood, however, that C-arm 1 may have any range of motion, and that different C-arms have potentially different ranges of motion. The instant invention is designed so as to not interfere with the range of motion of C-arm 1.

As further illustrated in FIG. 1, support 5 is connected to base 6. As shown, pool of bodily fluid 2 (e.g., blood) remains on the top of transmitter 3 following surgery on a patient. Previously, clean-up crews would simply sponge or wipe bodily fluid 2 from the C-arm 1. Another method of dealing with bodily fluid 2 would be to wrap the entire C-arm 1 in plastic wrap, or to wrap the entire C-arm 1 in bandages, mummy-style.

The prior art methods are problematic for at least two reasons. First, the prior art methods are invariably a two-person event, requiring multiple persons to stand on each side of C-arm 1 as the plastic wrap or mummy bandages are applied. Secondly, when blood dries on plastic wrap, some of the dried blood becomes airborne on removal of the plastic wrap.

The subject technology of the instant invention allows for safe, time-efficient clean-up of C-arm 1, as described in the following embodiments.

Figure 2:
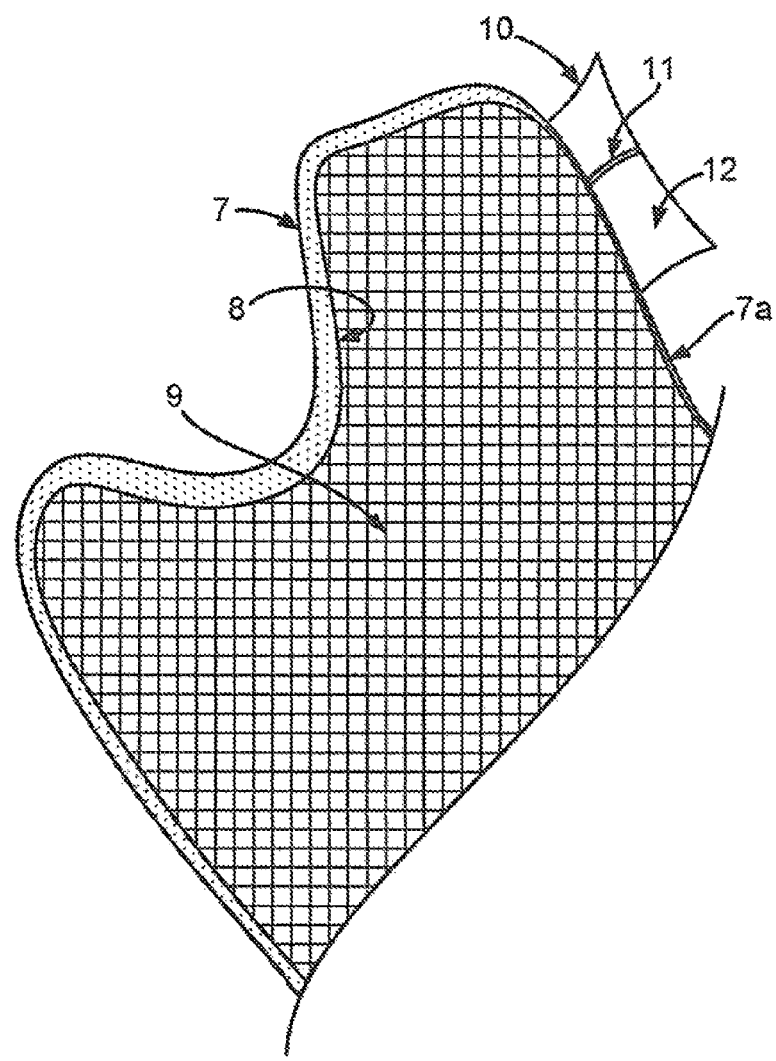
FIG. 2 is a medical equipment protective device in accordance with an embodiment of the subject technology.

FIG. 2 is an illustration of the subject technology showing a medical equipment protection device ("MEPD") with a first layer 7. First layer 7 comprises a flexible, fluid-absorbent material such as sterile cotton cloth or gauze. Also shown is edge 7a, second layer 8 with an adhesive face 9, and flexible wing edging 10. Flexible wing edging 10 serves as a "splatter shield," and includes structural support 11 and thin plastic 12. Structural support 11 may be metal and creates support for plastic 12 such that plastic 12 flairs out from an edge 7a of the MEPD. One or both of first layer 7 and second layer 8 may comprise a cross-hatch tear-resistant/rip-stop material for structural integrity of the MEPD.

Typically, flexible wing edging 10 is located on the MEPD where two transverse planes of medical equipment meet, such as a corner or an edge of a piece of medical equipment. Adhesive face 9 may comprise a sticky plastic that performs both a function of being a fluid barrier and the function of sticking to the surface of a piece of medical equipment, such as medical x-ray equipment with a C-arm 1. First layer 7 serves a function of absorbing bodily fluids, such as the bodily fluids shown in FIG. 1 that otherwise would have ended up on the medical equipment. First layer 7, second layer 8, and flexible wing edging 10 may be manufactured in a clean room/sterile environment utilizing layering techniques and/or seam sealing techniques such as heat-sealing, stitching and/or gluing.

Figure 3:
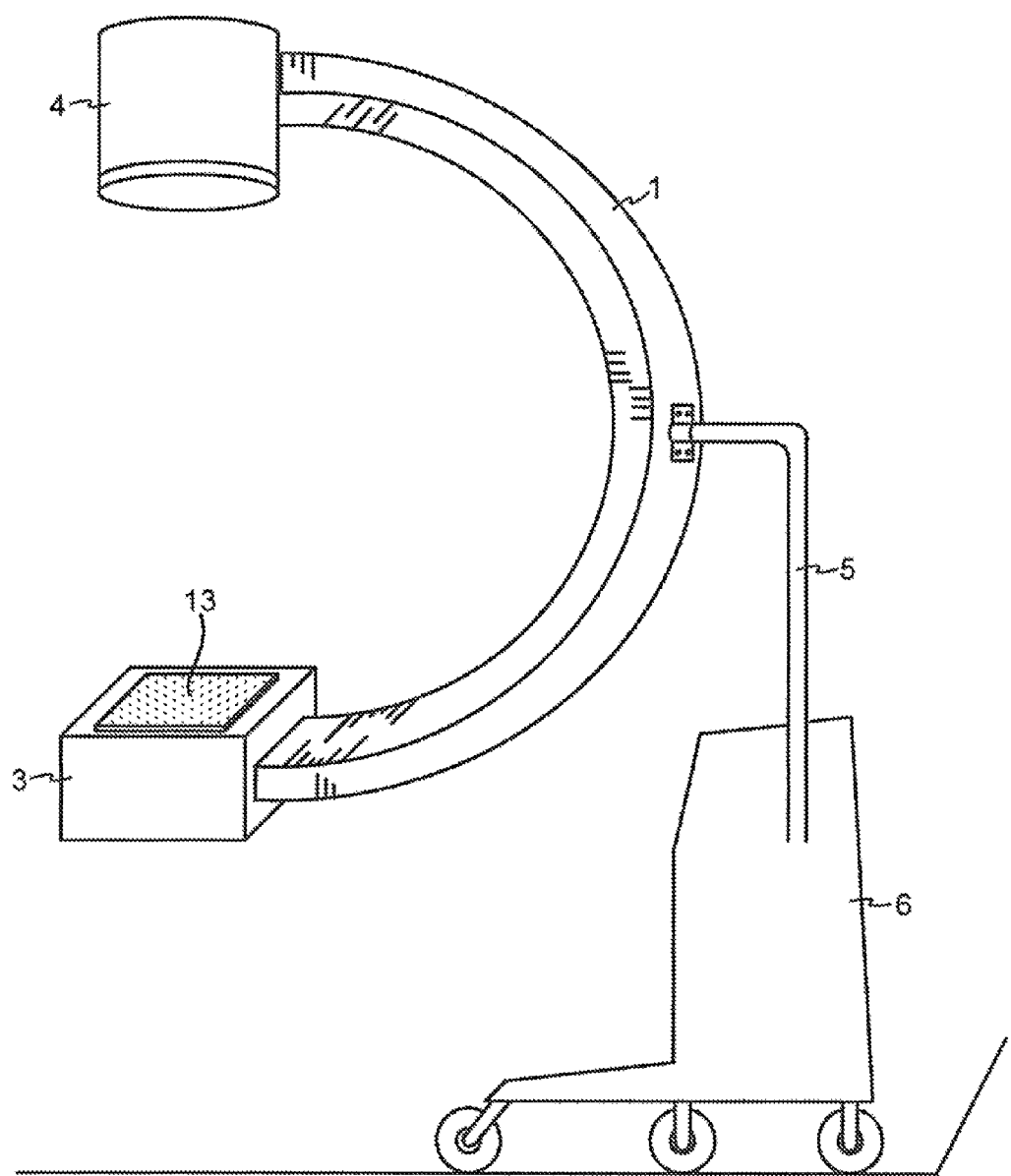
FIGS. 3-8 are illustrations of embodiments of the subject technology in use with a C-arm medical x-ray device.

FIG. 3 is an illustration of a C-arm 1 where the x-ray transmitter 3 is covered with an embodiment of the present invention, MEPD 13. MEPD 13 covers the transmitter 3 such that when a surgeon is operating on a patient and bodily fluid is released, the bodily fluid is absorbed into the MEPD 13. MEPD 13 has a bottom side that correlates to second layer 8 shown in FIG. 2. As such, the MEPD both adheres to the top side of transmitter 3 and prevents bodily fluid from reaching transmitter 3, as second layer 8 (as shown in FIG. 2) provides both an adhesive surface and a fluid barrier. The top side of MEPD 13 comprises first layer 7 (as shown in FIG. 2) with a flexible, fluid absorbent layer that absorbs the bodily fluid that drips from an operating table (not shown) onto MEPD 13.

Figure 4:
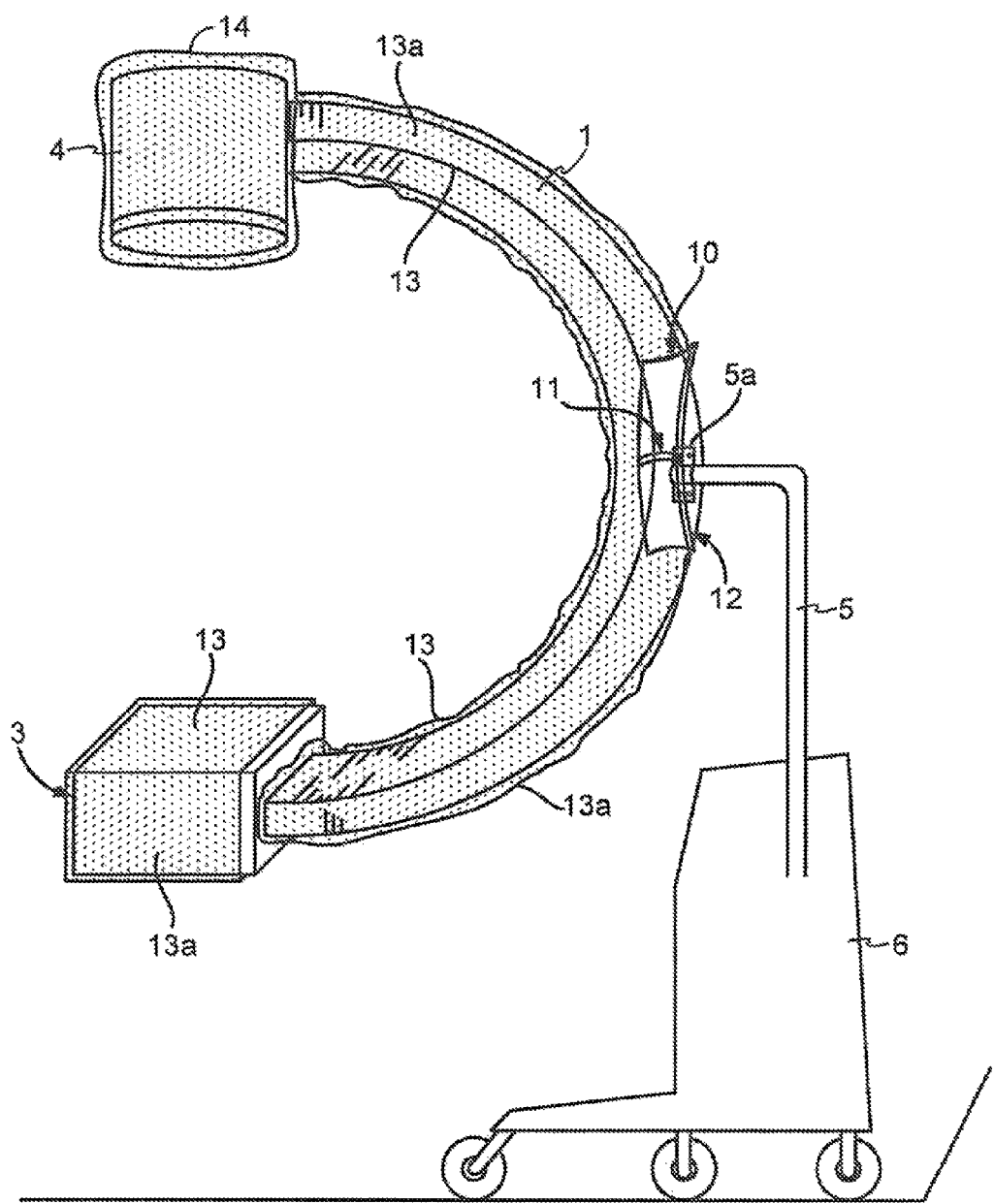

FIG. 4 is an illustration of a C-arm 1 where the x-ray transmitter 3 is encased on at least five sides (if not all six sides) with flank portions 13a. Flank portions 13a include both the first layer 7 and second layer 8, as described above. The flank portions 13a may fold out from a pre-packaged MEPD 13 that is designed and sized for any particular C-arm 1. MEPD 13 may be attached to all surfaces of C-arm 1 that could possibly end up beneath a patient and thereby potentially be exposed to bodily fluids. Flanking portions 13a, likewise, may be pre-configured to unfold along sides of C-arm 1 throughout any range of motion anticipated to possibly be exposed to bodily fluids.

Flexible wing edging 10, with structural support 11 and plastic 12, is configured to act as a splatter shield while also permitting viewing through itself so that an operator such as a surgeon can see through the splatter shield to handles 5a. Handles 5a are located on opposing sides of C-arm 1 and permit the operator to change the orientation of C-arm 1 to any desired position within the range of motion of the medical equipment. Plastic 12 may be a thin, clear plastic, or may be semi-opaque. Structural support 11 may be configured to be bent by the human hand, to thereby place flexible wing edging 10 at any desired angle and in various juxtapositions from C-arm 1 as desired.

Some embodiments may include the MEPD 13 including a "shower cap" or hood 14 that includes an elastic band to allow for easy coverage of image intensifier 4. In such embodiments, the MEPD 13 may initially be placed on x-ray transmitter 3 and unfolded along an inner side of C-arm 1 in a semi-circle until reaching image intensifier 4. Along the path of C-arm 1, flanking portions 13a and flexible wing edging 10 may be unfolded and placed in location using the adhesive side of layer 8 (shown in FIG. 2). Hood 14 may be located at either end of C-arm 1, may be made of thin plastic and may include a fluid absorbent exterior. In certain embodiments, hood 14 may be utilized for re-capture of a blood-soaked MEPD 13, where the MEPD 13 is folded in upon itself in the reverse of installation such that the MEPD 13 is bundled into hood 14 with nothing but second layer 8 and it's fluid barrier properties being exposed to a clean-up crew.

Such configurations permit both single-person application and removal, and permit for the safe and secure disposal of bodily fluids during the course of application and removal. Additionally, by not having to "mummy-wrap" C-arm 1 with either of plastic wrap or bandages, significant time is save.

Figure 5:
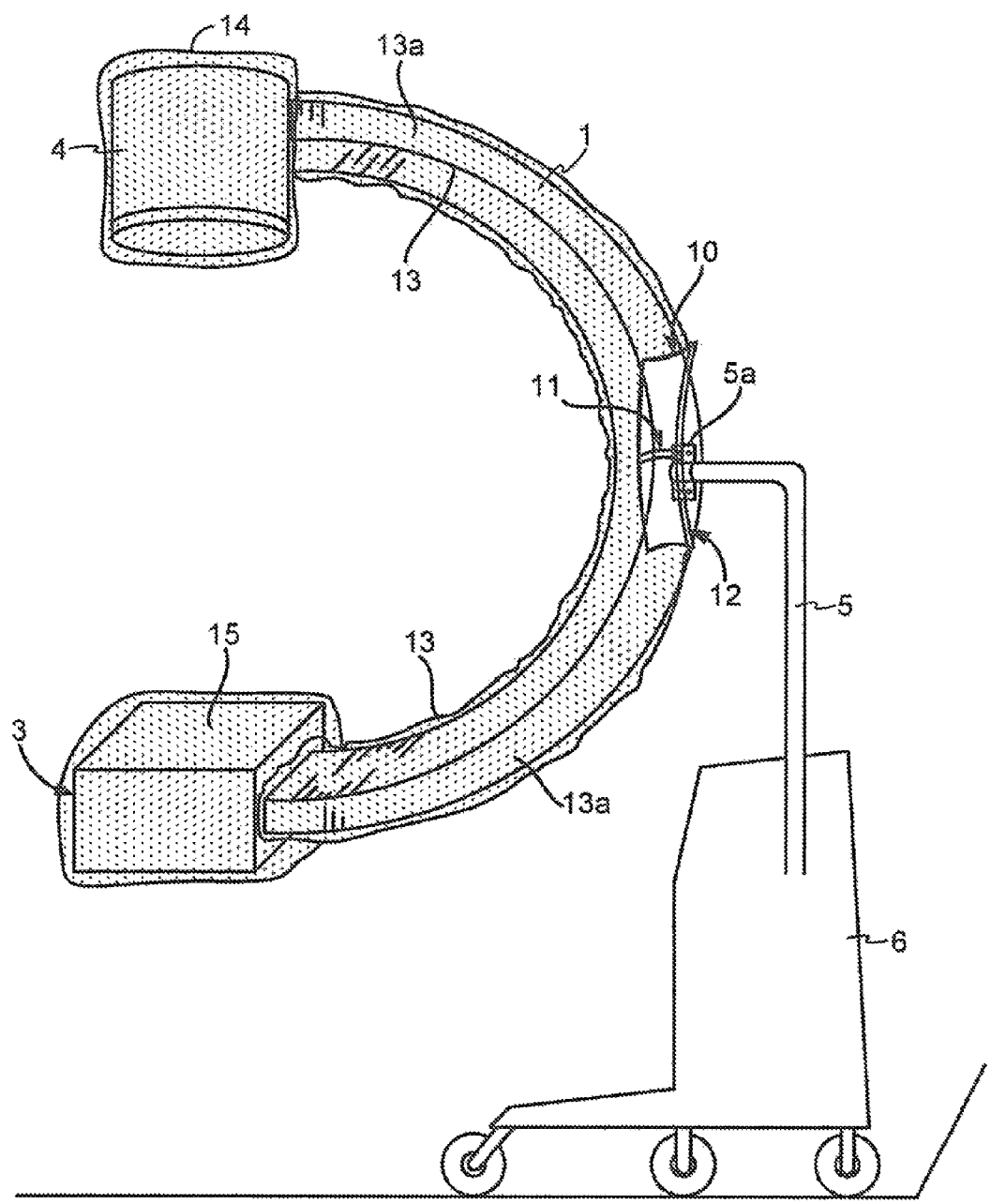

FIG. 5 is an illustration of an MEPD 13 where the configuration includes a sock 15 that simply slides over C-arm transmitter 3. Similar to hood 14, sock 15 may be located at either end of C-arm 1, may be made of thin plastic and may include a fluid-absorbent exterior. In certain embodiments, sock 15 may be utilized for re-capture of a blood-soaked MEPD 13, where the MEPD 13 is folded in upon itself in the reverse of installation such that the MEPD 13 is bundled into sock 15 with nothing but second layer 8 and it's fluid barrier properties being exposed to a clean-up crew.

Figure 6:
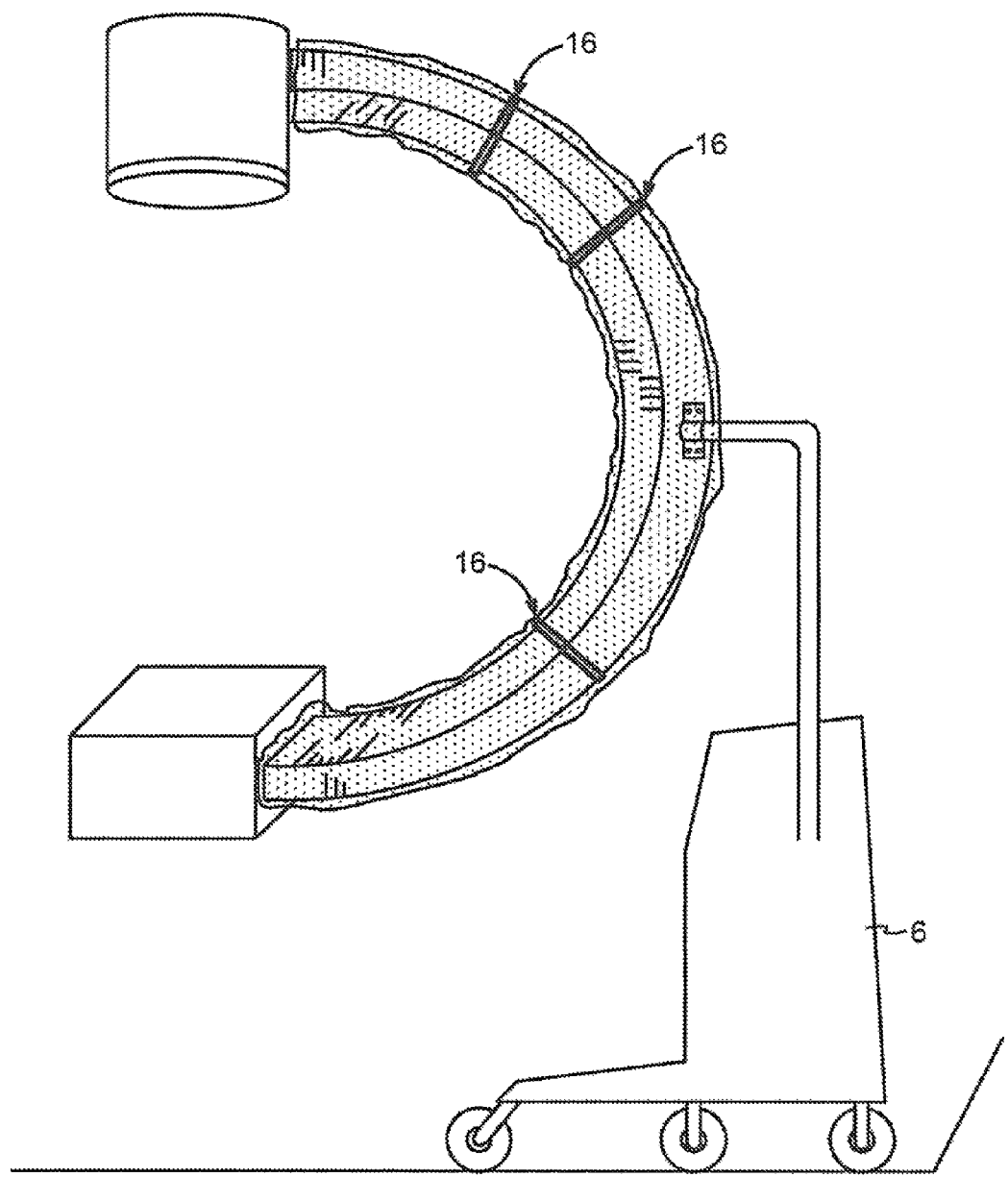

FIG. 6 is an illustration of an MEPD 13 where the configuration includes straps 16 for helping to secure the MEPD 13 in place. Straps 16 may be velcro, sticky tape, or hook and clasp, or other attachment means.

Figure 7:
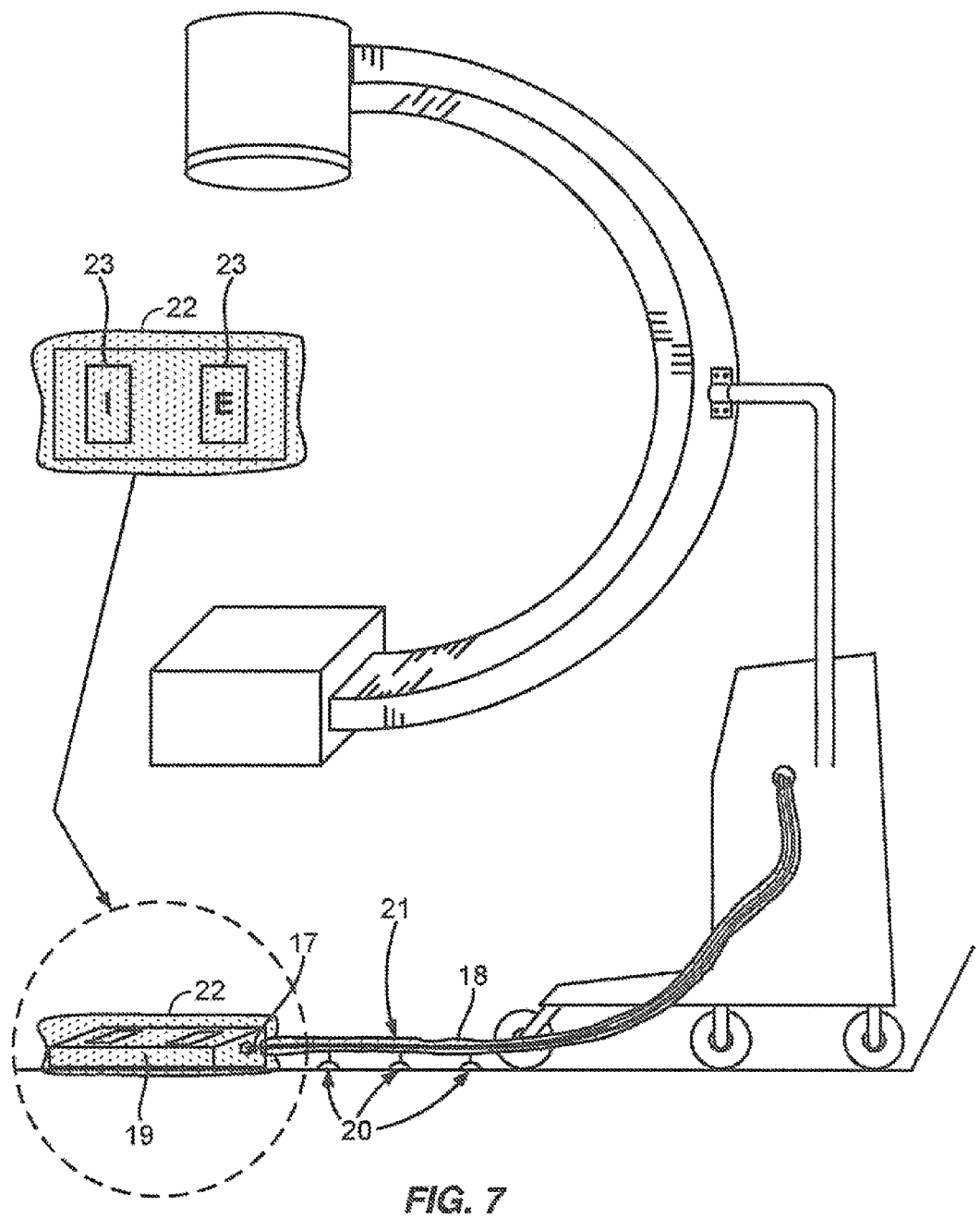

FIG. 7 is an illustration of an MEPD 13 and C-arm 1 including cabling 17 for footswitches 19. An operator may move the C-arm 1 into different positions, or may utilize the footswitches 19 for either more-precise and/or different angled viewing of an x-ray view provided by the medical equipment. Cabling 17 may be covered with tubular fluid barrier 18 which may have a fluid absorbent exterior 21. Cabling 17 may include suction cups 20 so that cabling 17 is temporarily fixed in position to the floor of an operating room. Footswitches 19 may be covered by cover 22. Cover 22 may be similar to a shower hood, and may be of a clear or colored plastic. In additional embodiments, cover 22 has a fluid absorbent layer and may have display a graphic tell the user what the switch is used for, for instance, whether the switch is for a different angle view or for zoom or to switch between views.

Figure 8:
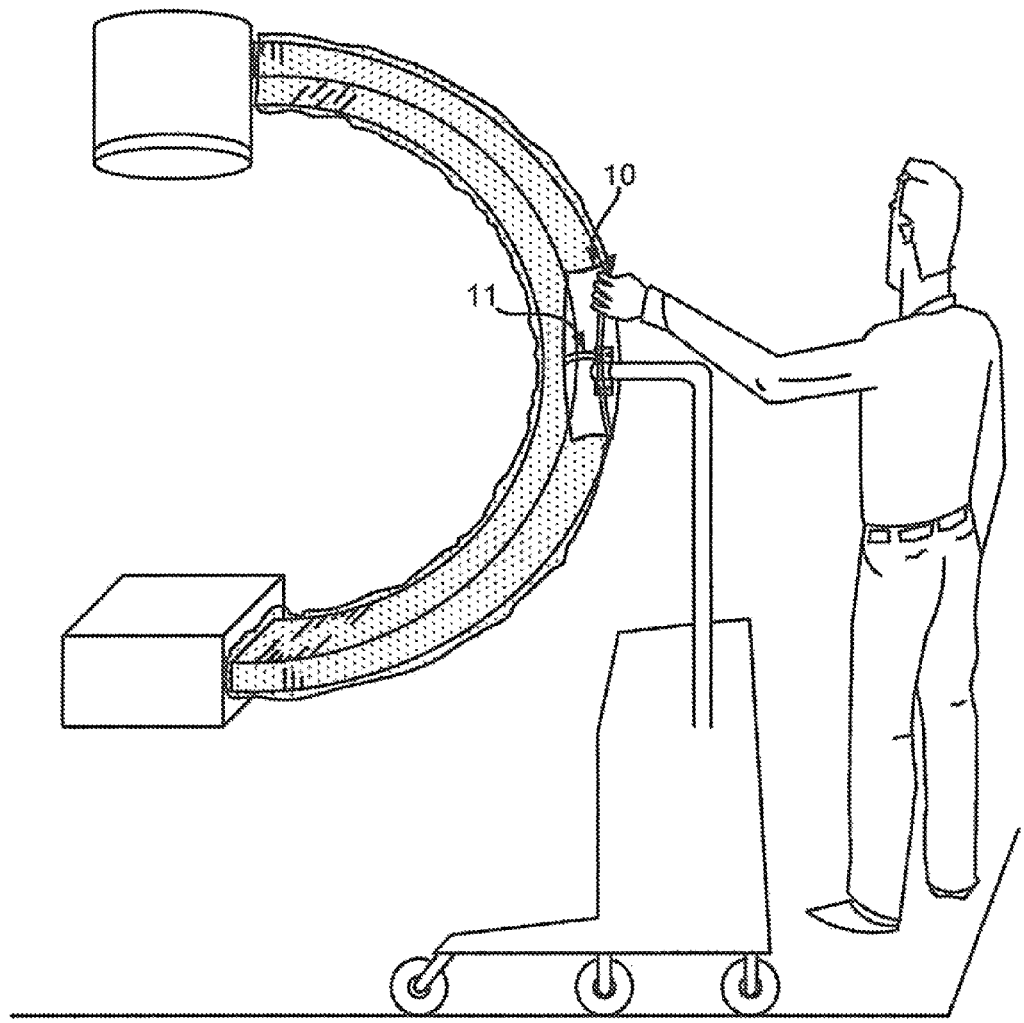

FIG. 8 is an illustration of a flexible wing edging 10 where a user is bending a support structure 11 by hand to place the flexible wing edging in a desired position.

The description of the subject technology is provided to enable any person skilled in the art to practice the various configurations described herein. While the disclosure has been particularly described with reference to the various figures and configurations, it should be understood that these are for illustration purposes only and should not be taken as limiting the scope of the subject technology.

There may be many other ways to implement the subject technology. Various functions and elements described herein may be partitioned differently from those shown without departing from the sprit and scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the spirit and scope of the subject technology.

It is understood that the specific order or hierarchy of steps or blocks in the processes disclosed is an illustration of exemplary approaches. Based upon design preferences, it is understood that the specific order or hierarchy of steps or blocks in the processes may be rearranged. The accompanying method claims present elements of the various steps in a sample order, and are not meant to be limited to the specific order or hierarchy presented.

The previous description is provided to enable any person skilled in the art to practice the various aspects described herein. Various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. §112, sixth paragraph, unless the element is expressly recited using the phrase "means for" or, in the case of a method claim, the element is recited using the phrase "step for."

All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

What is claimed is:

1. Medical equipment protection material for protecting medical equipment with at least one handle, comprising:
   a first layer comprising a flexible, fluid-absorbent material with at least one edge;
   a second layer comprising an adhesive face; and
   a flexible wing edging;
   wherein the first layer and the second layer are layered one atop the other such that the fluid-absorbent material is open-faced on a side opposite of the medical equipment protection material from the adhesive face of the second layer; and
   further wherein the flexible wing edging:
   (i) abuts the at least one edge and projects past the at least one edge;
   (ii) includes a clear plastic, and a structural support arm made of metal that is malleable by the human hand;
   (iii) is shape-retentive when bent;
   (iv) wherein the structural support arm supports the flexible wing edging past the at least one edge; and
   (v) is configured to act as a splatter shield for the at least one handle on the medical equipment.

2. The medical equipment protection material of claim 1, wherein:
   the clear plastic comprises a thin plastic film.

3. The medical equipment protection material of claim 1, wherein:
   the flexible wing edging abuts at least two edges of the fluid absorbent material, and
   the second layer along with the flexible wing edging comprises a contiguous liquid barrier.

4. The medical equipment protection material of claim 1, further comprising:
   flank portions of the medical protection material that cover side surfaces of medical equipment, the flank portions folding out or unrolling from a main portion of the medical protection material.

5. The medical equipment protection material of claim 4, wherein:
   the flank portions are connected with an elastic band that holds the flank portions against the side surfaces.

6. The medical equipment protection material of claim 4, wherein:
   the flank portions form a sock for holding the medical protection material.

7. The medical equipment protection material of claim 1, wherein:

the flexible wing edging projects past the at least one edge at least as far as the at least one handle extends from the medical equipment.

8. The medical equipment protection material of claim 1, further comprising:
a tubular fluid barrier for containing cords from the medical equipment.

9. The medical equipment protection material of claim 8, further comprising:
at least one suction cup for affixing the tubular fluid barrier to a surface.

10. The medical equipment protection material of claim 8, further comprising:
a fluid-absorbent material on an exterior surface of the tubular fluid barrier.

11. The medical equipment protection material of claim 8, further comprising:
fluid absorption material connected to an end of the tubular fluid barrier for covering foot switch controls connected to the medical equipment with the cords.

12. The medical equipment protection material of claim 11, further comprising:
a graphic on the fluid absorption material connected to the end of the tubular fluid barrier, the graphic noting a type of foot switch control.

13. The medical equipment protection material of claim 11, wherein:
the fluid absorption material connected to the end of the tubular fluid barrier is a bag that fits over the foot switch controls.

14. The medical equipment protection material of claim 1, wherein:
at least one of the first layer and the second layer comprises a rip-stop material with interwoven threads in a cross-hatch pattern.

15. The medical equipment protection material of claim 1, further comprising:
sterile packaging for storing the medical equipment protection material.

16. The medical equipment protection material of claim 1, further comprising:
at least one support strap for attaching the medical equipment protection material to the medical equipment.

17. The medical equipment protection material of claim 1, wherein:
the medical equipment includes the C-arm of a surgical x-ray machine.

* * * * *